Figures 1, 2:
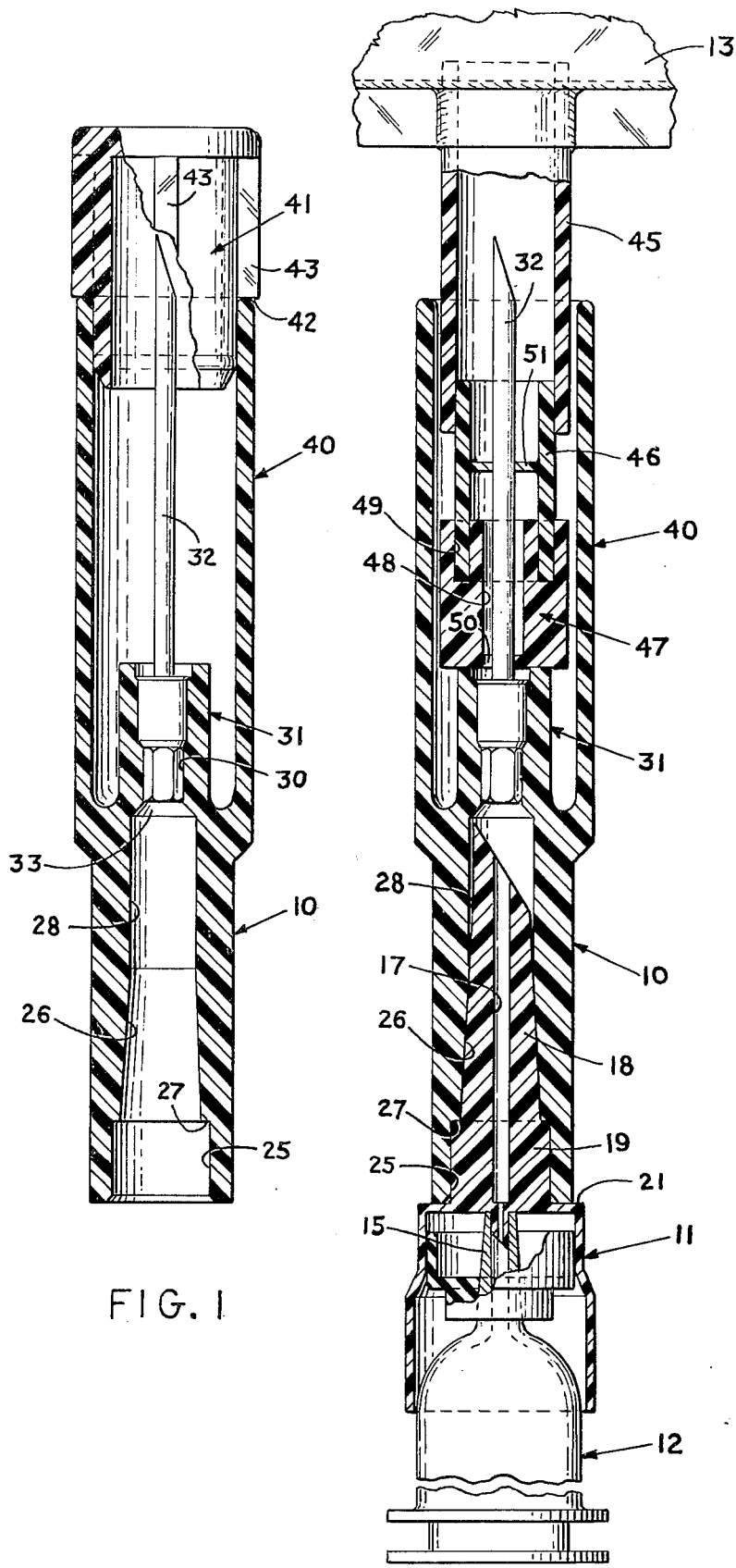

United States Patent [19]
Tischlinger

[11] 3,938,518
[45] Feb. 17, 1976

[54] SYRINGE ATTACHMENT DEVICE
[75] Inventor: Edward A. Tischlinger, Niantic, Conn.
[73] Assignee: Astra Pharmaceutical Products Inc., Worcester, Mass.
[22] Filed: Jan. 15, 1975
[21] Appl. No.: 541,205

[52] U.S. Cl. ............................ 128/272; 128/218 NV
[51] Int. Cl.² ............................................. A61J 1/00
[58] Field of Search ........... 128/272, 221, 216, 215, 128/218, DIG. 26, DIG. 28, 220

[56] References Cited
UNITED STATES PATENTS

| | | | |
|---|---|---|---|
| 2,724,383 | 11/1955 | Lockhart | 128/215 |
| 3,826,260 | 7/1974 | Killinger | 128/272 |
| 3,826,261 | 7/1974 | Killinger | 128/272 |
| 3,872,867 | 3/1975 | Killinger | 128/272 |

Primary Examiner—John D. Yasko
Attorney, Agent, or Firm—John J. Hart

[57] ABSTRACT

The attachment unit for a spike equipped syringe is composed of first and second tubular portions connected together at their inner ends and extending from such connection in axially aligned relation. The bore of the first tubular portion has at its outer end a cylindrically shaped seat for the hub of the spike, and adjacent to such cylindrical seat a conical seat for the spike, the two seats forming between them an internal shoulder to properly register the spike in such first tubular portion. Connected at its inner end to said connection and enclosed in the inner end of the second tubular portion is a tubular needle mounting, the bore of which is in communication with the bore of the first tubular portion. One end of a needle cannula is secured in liquid-tight relation in the mounting bore and the cannula extends from such mounting and through the bore of the second tubular portion to a point beyond the outer end of such second tubular portion. The projecting end of the cannula is enclosed by a cup-shaped cap which fits on the outer end of the second tubular portion and is provided with a stop flange engageable with such outer end of the second tubular portion to prevent the needle engaging the closed end of the cap.

4 Claims, 2 Drawing Figures

SYRINGE ATTACHMENT DEVICE

This invention relates to a device for attachment to a syringe provided with a transfer spike.

Syringes of the indicated type are commonly employed for the packaging of a drug solution such as a concentrated additive solution to be introduced into solutions for intravenous therapy. The transfer spike which is usually a large plastic hollow instrument, is frequently employed on syringes filled with additives to facilitate a rapid transfer of the contents of such syringes, and also to prevent an inadvertent administration of the additive solution directly into a vein. Heretofore, intravenous solutions, such as physiological saline or glucose, were usually packaged in bottles with rubber closures which also serve as entry or dispensing ports and can be pierced by either a hypodermic needle or the aforesaid plastic spike for the purpose of introducing the additives into the intravenous solutions.

Recently there has been an increase in the use of plastic bags as containers for intravenous solutions. These plastic bags are generally provided at their bottoms with depending teat-like, dispensing and entry ports which are of such small dimensions that they will not accept a transfer spike. Accordingly, when an additive is packaged in a syringe equipped with a spike, it is usually necessary to transfer the additive from such syringe to a syringe having a hypodermic needle and then use the latter to discharge the additive into the solution contained in a plastic bag through one of its depending ports.

The principal object of the present invention is to provide an attachment for a transfer spike equipped syringe so as to enable the latter to asceptically transfer its contents directly into solutions contained in any type of bottle or plastic bag medicament container.

Another object of the invention is to provide an inexpensive, disposable unit capable of being readily attached to a plastic transfer spike provided on a syringe containing an intravenous additive and when so attached providing a suitable needle for the aseptic transfer of the additive directly into a solution contained in any type of intravenous solution container.

Other objects of the invention, as well as the advantages and novel features thereof will become apparent from a perusal of the following description when read in connection with the accompanying drawings, in which FIG. 1 is a vertical sectional view showing the attachment unit of this invention in the form it will be packaged; and FIG. 2 is a similar view showing the unit of FIG. 1 attached to a common form of syringe spike and mounted on a known plastic bag entry port for transfer of the additive contained in the syringe into the intravenous solution contained in the plastic bag.

As is shown in the drawings, the attachment unit of this invention is generally tubularly-shaped and made of an integral piece of plastic or other suitable material. The integral plastic device illustrated comprises an end portion 10 for attachment to a known transfer spike 11 provided on a known type of disposable syringe 12 containing the additive to be discharged into the intravenous solution contained in either the usual type of bottle or plastic bag 13 used for this purpose. The spike 11 is usually made of a suitable plastic material such as "Delrin" and is constructed to readily form a tight seal when attached to the discharge nozzle 15 of a syringe and to bring this into communication with an enlarged passage 17 extending longitudinally through the needle-shaped, tapered, working end 18 of the transfer spike. In the example illustrated, the tapered needle-shaped end 18 of the spike is integral with a cylindrically shaped hub portion 19.

The spike attachment end portion 10 of the device or unit of this invention has a generally cylindrical external configuration of substantially uniform diameter, but the inner bore or longitudinally extending passageway through such end portion 10 is variably shaped. In the example shown, the outer end portion 25 of such passageway is cylindrically shaped and of such length and diameter that the entire spike hub portion 19 is snugly received therein with the shoulder 21 at the outer end of such hub portion 19 abutting against the terminal end of the attachment end portion 10, as shown in FIG. 2 of the drawings. The portion 26 of the passageway adjacent to such cylindrically shaped portion 25 is conically shaped to provide a seat for the tapered portion of the spike needle end 18 which is adjacent to the hub 19. The outer end of the passage portion 26 has a diameter less than that of passage portion 25 so that an internal annular shoulder 27 is formed at the inner end of the passage portion 25. The internal shoulder 27 coacts with the shoulder 21 to properly position the hub portion 19 with respect to the attachment end portion 10. The inner portion 28 of the passageway through the attachment end portion 10 extends from the inner end of the conical seat 26 to a point beyond the piercing end of the spike 18 and is cylindrically shaped with a diameter greater than the exterior dimensions of the piercing end of the spike 18.

The inner end of passageway portion 28 communicates with one end of a reduced passage 30 extending through an internal tubularly shaped mounting 31 for a piercing or penetrating needle 32. The mounting 31 is integrally connected at its base end to the inner end of the attachment end portion 10 and projects outwardly from such connection and in aligned relation with such end portion 10 so as to be in effect an extension of the latter. The passages through the end portion 10 and mounting 31 are axially aligned and are connected by a conically shaped reduction 33 at the terminal inner end of passageway portion 28. Located in the passage 30 adjacent to the reduced terminal passage portion 33 is a hypodermic type of needle 32. The needle 32 is permanently secured in passage 30 by molding or otherwise fixing it in a manner known to the art. The inner end of the needle cannula is thus secured in liquid-tight relation in the passage 30 but with its bore in communication with the passageway portion 28.

Surrounding the mounting 31 and in spaced relation thereto is an elongated, tubular end portion 40 which is integrally connected at its inner end to the inner end of end portion 10 and to the connected end of the mounting 31. The tubular end portion 40, end portion 10 and the mounting 31 have a common central longitudinal axis. The end portion 40 is substantially cylindrically shaped throughout its length and has a substantially uniform internal diameter approximating the external diameter of the end portion 10. The end portion 40 extends from the base of the mounting 31 to a point substantially beyond the outer projecting end of such mounting, but short of the piercing end of the needle 32 so that the latter projects beyond the outer end of such attachment end portion 40. For purposes of sterility and as a protection against such projecting end of the needle during the handling of the attachment, the outer end of the attachment end portion 40 is fitted with a protective cap 41. The cap 41 is constructed to enable its open end to be inserted into the open outer end of end portion 40 in the manner of a stopper and is provided with an outer shoulder 42 which may be formed by the ends of a plurality of longitudinally extending beads or ribs 43 so as to afford a more secure grip for manipulation of the cap. The shoulder 42 whether continuous, or interrupted by ribs 43 as shown, is located so that the cap is prevented from being inserted into the attachment portion 40 to the extent that the piercing end of the needle 32 will come into contact with the outer end wall of the cap.

As previously indicated, the type of plastic bag 13 which serves as a container for an intravenous solution is generally hung on a standard when in use and is provided at its lower end with a plurality of depending, teat-like dispensing and entry ports, such as the teat-like, integral, tubular projection 45 shown in FIG. 2. of the drawings. The projection 45 which is utilized as an entry port has inserted into its end and bonded thereto in a known manner one end of a short, plastic, tubular member 46 which serves as a nozzle or extension for the projection 45. The tubular member or nozzle 46 is closed at its outer end by a cylindrical cap 47 made of soft pliable plastic such as rubber. The cap 47 has a central passageway 48 of a diameter greater than the external diameter of the needle 32 and has at its open end an annular recess 49 which surrounds the passageway 48 and into which the outer end of the nozzle 46 is inserted in liquid-tight relation. The head or outer end of the cap 47 is formed to close the passageway 48 with a thin layer 50 of material that may be readily pierced by the piercing end of the needle 32, and hold the needle in liquid-tight relation.

It will be understood from the foregoing, that when the device of this invention is attached to a spike on an additive syringe in the manner previously described, the syringe may readily be connected to a plastic intravenous solution bag 13 by inserting an entry port 45 thereof into the open end of the attachment portion 40 until the cap 47 seats on the projecting end of the needle mounting 31 as is illustrated in FIG. 2 of the drawings. As the cap 47 is being inserted into the attachment portion 40, the sharp end of needle 32 will pierce the thin layer or diaphragm 50 of the cap and penetrate up through the extension 46 and into the entry port 45. In its passage through the extension 46 of the entry port, the needle penetrates a diaphragm 51 formed in such extension and functioning as a seal preventing the entry of the intravenous solution in the bag 13 into the cap 47. Thus, there is little or no medicinal material in the extension 46 and cap 47 between the diaphragms 51, 50, respectively, thereof during the transfer of the additive from the syringe 12 into the intravenous solution contained in the bag 13. It will be seen therefore, that the present invention provides an attachment which enables the ready aseptic transfer of additives directly into an intravenous solution plastic bag from a spike equipped syringe. Since the one type of syringe can thus be readily utilized with any type of the presently used intraveneous solution containers, it will be evident that use of the attachment of this invention will effect a substantial saving in time and expense to nurses and hospitals.

What is claimed is:

1. An attachment unit for medicinal syringes equipped with a transfer spike comprising first and second elongated tubular portions connected together at their inner ends and extending from such connection in axially aligned, opposed directions so that said first tubular portion provides at one end of the unit an entry passage for a syringe spike and said second tubular portion provides at the other end of the unit an entry passage for a tubular entry port of the plastic bag for medicinal material, the bore of said first tubular portion being formed at its outer end portion to provide a first seat snugly receiving one part of a syringe spike and adjacently to said outer end portion being formed to provide a second seat for another part of the spike, an internal shoulder formed in such bore between said first and second seats to properly register said spike parts on said seats, the bore of said first tubular portion having a length greater than the length of the spike insertable thereinto, tubular means providing a reduced passageway axially aligned with the bores of said first and second tubular portions and communicating at one end with the inner end of the bore in said first tubular portion, a needle cannula having one end located in said reduced passageway with its bore in communication with said first tubular portion bore, means for mounting said one end of the needle cannula in liquid-tight relation in said reduced passageway and with the remainder of said needle extending outwardly therefrom axially through the bore of said second tubular portion, the bore of said second tubular portion being formed to receive the tubular entry port of a plastic medicinal bag with such remainder of the needle extending through the bore of such port, and the outer end of said tubular means providing a stop seat for the terminal outer end of such entry port.

2. An attachment as defined in claim 1, in which said first seat in the bore of said first tubular portion is cylindrically shaped, and the second seat in such bore is conically-shaped and terminates at a point spaced from the inner end of such bore, the outer end greater said second seat at said internal shoulder having a graeter diameter than the inner end of said second seat.

3. An attachment as defined in claim 1, in which said tubular means has an exterior diameter less than the internal diameter of the bore of said second tubular portion so that the exterior surface of said tubular means is spaced from the inner wall of such bore by an annular recess in communication at its outer end with the portion of the bore of said second tubular portion beyond the outer end of said tubular means.

4. An attachment as defined in claim 1, in which said needle cannula projects beyond the outer end of said second tubular portion, said unit including a cup-shaped cap having an open end portion engageable with the outer end of said second tubular portion to enclose the projecting portion of said cannula, and having stop means engageable with the terminal end of said second tubular portion to register said cap on said second tubular portion.

* * * * *